US009454699B2

(12) United States Patent
Agrawal et al.

(10) Patent No.: US 9,454,699 B2
(45) Date of Patent: Sep. 27, 2016

(54) HANDLING GLARE IN EYE TRACKING

(71) Applicant: MICROSOFT TECHNOLOGY LICENSING, LLC, Redmond, WA (US)

(72) Inventors: Mudit Agrawal, Redmond, WA (US); Vaibhav Thukral, Kirkland, WA (US); Ibrahim Eden, Kirkland, WA (US); David Nister, Bellevue, WA (US); Shivkumar Swaminathan, Woodinville, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 107 days.

(21) Appl. No.: 14/264,952

(22) Filed: Apr. 29, 2014

(65) Prior Publication Data
US 2015/0310253 A1    Oct. 29, 2015

(51) Int. Cl.
*G06K 9/00* (2006.01)
*G06K 9/52* (2006.01)
(Continued)

(52) U.S. Cl.
CPC ............ *G06K 9/0061* (2013.01); *G06F 3/013* (2013.01); *G06K 9/00604* (2013.01);
(Continued)

(58) Field of Classification Search
CPC ........... G06K 9/0061; G06K 9/00624; G06K 9/4661; G06K 9/52; G06K 9/6201; G06K 9/00604; H04N 5/33; G06F 3/013
USPC ....................................................... 382/103
See application file for complete search history.

(56) References Cited

U.S. PATENT DOCUMENTS 6,152,563 A    11/2000  Hutchinson et al.
6,714,665 B1    3/2004  Hanna et al.
(Continued)

FOREIGN PATENT DOCUMENTS

EP    1655687 A2    5/2006
WO    2012047221 A1    4/2012
WO    2012177542 A1    12/2012

OTHER PUBLICATIONS

Zhu, et al., "Robust Real-Time Eye Detection and Tracking Under Variable Lighting Conditions and Various Face Orientations", In Journal of Computer Vision and Image Understanding, Apr. 2005, 31 pages.
(Continued)

*Primary Examiner* — Tom Y Lu
(74) *Attorney, Agent, or Firm* — Dave Ream; Tom Wong; Micky Minhas

(57) ABSTRACT

Embodiments are disclosed for eye tracking systems and methods. An example eye tracking system comprises a plurality of light sources and a camera configured to capture an image of light from the light sources as reflected from an eye. The eye tracking system further comprises a logic device and a storage device storing instructions executable by the logic device to acquire frames of eye tracking data by iteratively projecting light from different combinations of light sources of the plurality of light sources and capturing an image of the eye during projection of each combination. The instructions may be further executable to select a selected combination of light sources for eye tracking based on a determination of occlusion detected in the image arising from a transparent or semi-transparent optical structure positioned between the eye and the camera and project light via the selected combination of light sources for eye tracking.

15 Claims, 8 Drawing Sheets

(51) Int. Cl.
*G06K 9/46* (2006.01)
*G06K 9/62* (2006.01)
*H04N 5/33* (2006.01)
*G06F 3/01* (2006.01)

(52) U.S. Cl.
CPC ....... *G06K 9/00624* (2013.01); *G06K 9/4661* (2013.01); *G06K 9/52* (2013.01); *G06K 9/6201* (2013.01); *H04N 5/33* (2013.01)

(56) References Cited

U.S. PATENT DOCUMENTS

| | | | |
|---|---|---|---|
| 7,630,002 | B2 | 12/2009 | Jenkins |
| 8,324,602 | B2 | 12/2012 | Wiese et al. |
| 8,878,749 | B1* | 11/2014 | Wu .................... G01S 17/06 345/8 |
| 2007/0189606 | A1 | 8/2007 | Ciuc et al. |
| 2011/0170060 | A1 | 7/2011 | Gordon |
| 2011/0305388 | A1 | 12/2011 | Wedi et al. |
| 2012/0105486 | A1 | 5/2012 | Lankford et al. |
| 2012/0133891 | A1 | 5/2012 | Jiang |
| 2012/0229681 | A1 | 9/2012 | Ansfield et al. |
| 2013/0114850 | A1 | 5/2013 | Publicover et al. |
| 2013/0135198 | A1 | 5/2013 | Hodge et al. |
| 2013/0285901 | A1 | 10/2013 | Lee et al. |
| 2014/0204029 | A1* | 7/2014 | Lopez .................. G06F 3/013 345/163 |
| 2014/0375541 | A1* | 12/2014 | Nister .................. G06F 3/013 345/156 |
| 2015/0199006 | A1* | 7/2015 | He ...................... A61B 3/113 345/158 |

OTHER PUBLICATIONS

Bialkowski, et al., "A Non-Intrusive Approach to Gaze Estimation", In Proceedings of the 8th International Conference on Computer Vision, Pattern Recognition, and Image Processing, Jul. 18, 2007, 4 pages.

Ji, et al., "Real-Time Eye, Gaze, and Face Pose Tracking for Monitoring Driver Vigilance", In Journal Real-Time Imaging vol. 8 Issue 5, Oct. 2002, 21 pages.

Bohme, et al., "Remote Eye Tracking: State of the Art and Directions for Future Development", In Proceedings of the 2nd Conference on Communication by Gaze Interaction, Sep. 4, 2006, 5 pages.

Hennessey, et al., "Improving the Accuracy and Reliability of Remote System-Calibration-Free Eye-gaze Tracking", In IEEE Transactions on Biomedical Engineering, vol. 56, Issue 7, Jul. 2009, 10 pages.

Martinez, et al., "Rendering Optimizations Guided by Head-Pose Estimates and their Uncertainty", In Proceedings of the First international conference on Advances in Visual Computing, Dec. 5, 2005, 10 pages.

Jo, et al., "A Robust Gaze Tracking Method for Users Wearing Glasses", In Proceedings of Advanced Science and Technology Letters vol. 43, Retrieved on: Dec. 18, 2013, 31 pages.

ISA European Patent Office, International Search Report and Written Opinion Issued in PCT Application No. PCT/US2015/027185, Aug. 13, 2015, WIPO, 20 pages.

IPEA European Patent Office, International Preliminary Report on Patentability Issued in PCT Application No. PCT/US2015/027185, Jan. 27, 2016, WIPO, 8 Pages.

* cited by examiner

FRONT VIEW

OBLIQUE VIEW

HANDLING GLARE IN EYE TRACKING

BACKGROUND

Users may interface with computing systems using a variety of input mechanisms. For example, eye gaze tracking may be utilized to interact with a graphical user interface, wherein a determined location at which a user's gaze intersects the graphical user interface may be used as a positional signal for interactions with the user interface. Gaze tracking techniques may employ one more light sources to project light onto an eye, and one or more cameras to capture images of glints of the projected light as reflected from the eye. The locations of the glints and/or the pupil in the images may be utilized to determine a pupil position indicating a gaze direction.

SUMMARY

Embodiments are disclosed that relate to performing eye gaze tracking in the presence of sources of glare, such as eyeglasses located between an eye tracking camera and an eye being tracked. For example, in one embodiment, an example eye tracking system comprises a plurality of light sources and a camera configured to capture an image of light from the light sources as reflected from an eye. The eye tracking system further comprises a logic device and a storage device storing instructions executable by the logic device to acquire frames of eye tracking data by iteratively projecting light from different combinations of light sources of the plurality of light sources and capturing an image of the eye during projection of each combination. The instructions may be further executable to select a selected combination of light sources for eye tracking based on a determination of occlusion detected in the image arising from a transparent or semi-transparent optical structure positioned between the eye and the camera and project light via the selected combination of light sources for eye tracking.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

In an eye tracking system, camera(s) and/or light source(s) may be positioned in a location that is spaced from the eye and/or head of the user. Thus, objects may be present between the camera(s)/light source(s) and the eye, such as glasses, which may produce additional reflections of light projected by the light sources. These reflections may appear as glares in an image, and may occlude one or more of the glints and/or the pupil. Thus, such glares may interfere with eye tracking.

As occlusion of eye tracking glints by such glares and other spurious reflections may vary with position and/or orientation of a user relative to the glint light source(s) and camera(s), different light source configurations and different types and/or thicknesses of glasses may produce different glare locations. Thus, embodiments are disclosed that relate to projecting different configurations of light sources to help identify a light source configuration that allows eye tracking to be performed without unacceptable occlusion of eye glints from glares caused by glasses and the like.

Figure 1:
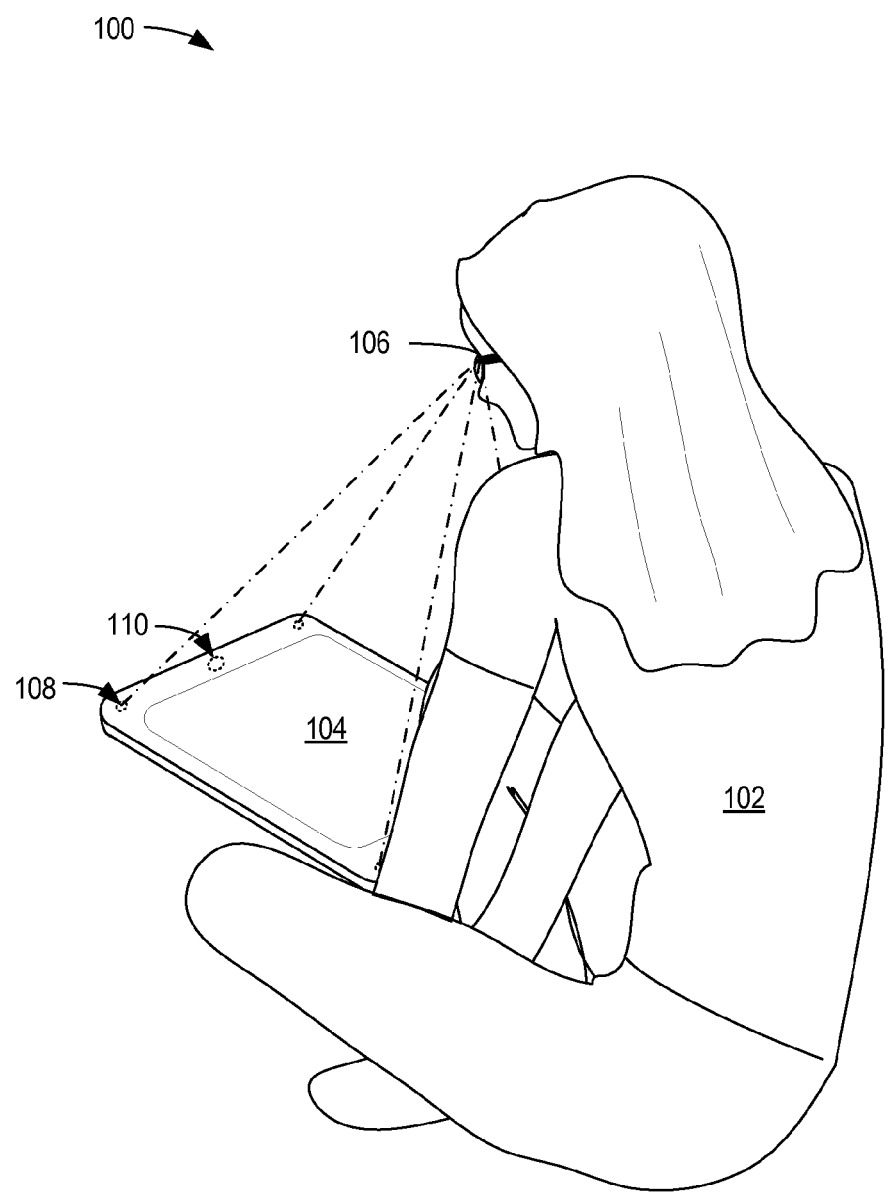
FIG. 1 shows an embodiment of an example eye tracking environment.

FIG. 1 shows an example eye tracking environment 100 in which a user 102 is viewing a computing device 104 while wearing glasses 106. The computing device 104 is depicted as a tablet, but it will be understood that any other suitable computing device may utilize eye tracking. Examples include, but are not limited to, smart phones, laptops, personal computers, televisions, and wearable computing devices such as head-mounted display devices.

Computing device 104 includes an eye tracking system comprising a plurality of light sources 108 and a camera 110. Light sources 108 may comprise, for example, a plurality of light emitting diodes (LEDs), and/or other suitable light emitting devices. In some embodiments, the light sources 108 may emit infrared light, visible light, or combinations of visible and infrared light (e.g., a subset of the light sources 108 may project infrared light and another subset of the light sources 108 may project visible light). The camera 110 may comprise any suitable imaging device, including but not limited to a depth camera, an RGB (color imaging) camera, a grayscale camera, a stereo camera pair, and/or any other suitable camera or combination of cameras. It will be understood that one or more of the light sources, the camera(s), and/or any other element of the eye tracking system may be integrated within a single computing device, housed separately from the computing device, or arranged in any combination thereof.

As illustrated by the dashed lines in FIG. 1, each light source 108 may emit light toward an eye of the user 102. The camera 110 may capture images of the eye of the user 102 that include reflections from the eye of the light projected from the light sources 108. Based on a location of the reflections of the projected light in the image from the camera 110 compared to a pupil (or iris, or other suitable eye structure) of the user's eye, a direction of gaze may be determined. This may allow a gaze to be projected from the eye, such that a location at which the projected gaze intersects a user interface or a real-world object may be determined. This may allow a user to interact with a computing device via gaze. Further, changes in gaze location over time may be used as gesture inputs for a computing device.

Figure 2:
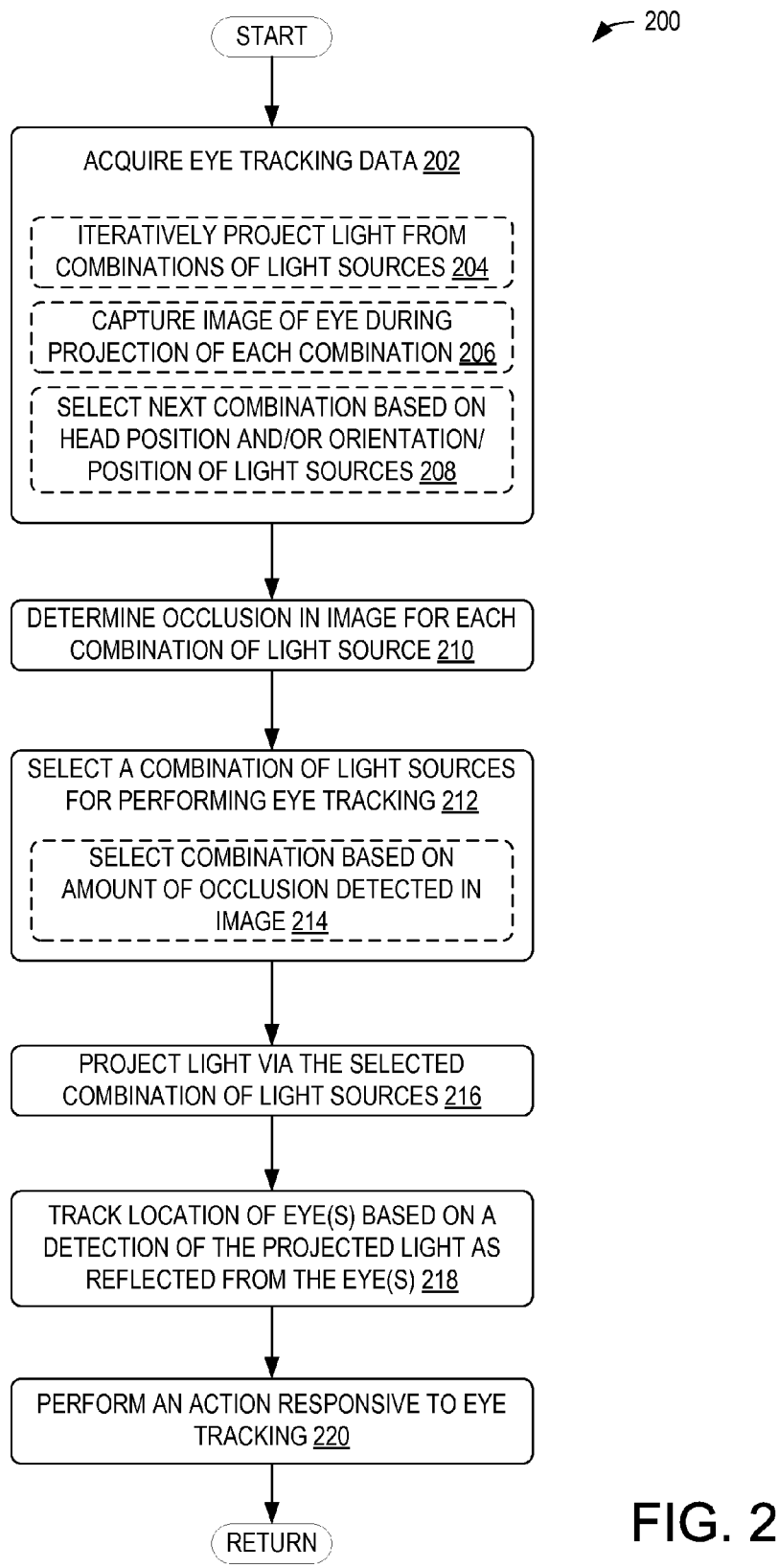
FIG. 2 is a flow diagram depicting an embodiment of a method of sequencing light sources in an eye tracking system.

FIG. 2 shows a flow diagram depicting an embodiment of a method 200 for tracking eye movements that may help to achieve robust eye tracking performance in the presence of glasses or other such structure between the light source(s)/camera(s) and the user's eye. Method 200 may be performed by an eye tracking system in a computing device, such as computing device 104 of FIG. 1.

At 202, method 200 includes acquiring eye tracking data. As described above, eye tracking may be performed by emitting light (e.g., infrared light) toward eye of a user and capturing images of the light as reflected from the eye of the user. However, as light also may be reflected from eyeglasses or other transparent or semi-transparent optical structures between the light sources and the user's eye, glares may arise that occlude the reflections of the light from the user's eye.

Figure 8:
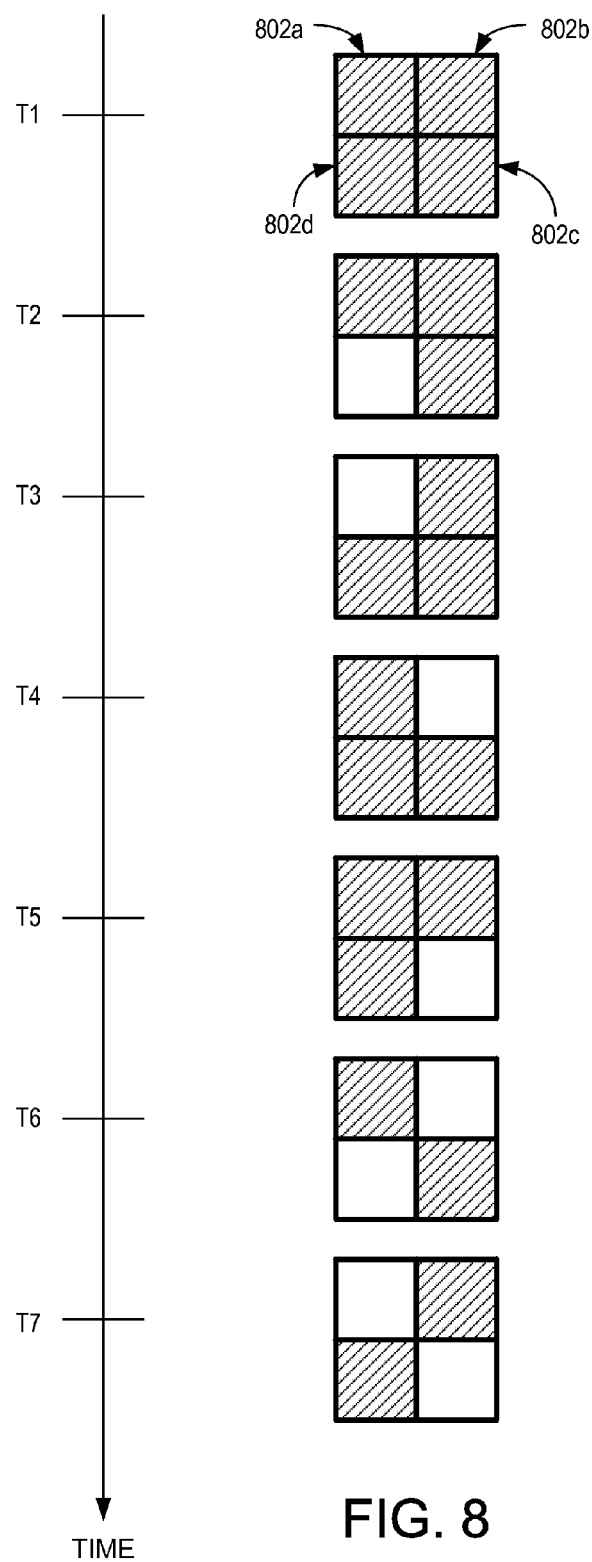
FIG. 8 shows an example sequence of light source according to an embodiment of the present disclosure.

Thus, as indicated at 204, method 200 may include iteratively projecting light from different combinations of light sources, and at 206, capturing an image of the eye during the projection of each different combination of light sources, as indicated at 206. These processes may involve, for example, projecting light from different numbers of light sources in the different combinations and/or projecting light from light sources having different positions/orientations. As a more specific example, FIG. 8 schematically illustrates an eye tracking system that include four light sources 802a-802d, wherein illuminated light sources are shown by diagonal lines within a box representing a light source. Iteratively projecting light from different combinations of light sources may include projecting light from all light sources, (as shown at time T1); then from different combinations of three light sources (as shown at times T2, T3, T4, and T5); and then from different combinations of two light sources (as shown at times T6 and T7) or just one light source (not shown in the Figure). It is to be understood that such a cycle of light source projections may be performed in any suitable order. For example, combinations with greater numbers of light sources illuminated may be tried before those with lesser numbers of light sources where a most accurate gaze determination is desired, while those with lesser numbers may be tried before those with greater numbers where power savings is desired, or where the glass surfaces tend to produce more glares.

Further, in some embodiments, an order of combinations of light sources to project may optionally be selected based on a head/HMD position and/or an orientation/position of the light sources, as indicated at 208. For example, it may be known that particular numbers and/or patterns of light sources may produce fewer occlusions when a head is positioned at a given angle. By selecting a next combination based on the above-described information, the different combinations of light sources may be iteratively cycled in an intelligent manner to increase the likelihood that a suitable combination of light sources may be utilized in an early iteration, thereby reducing the amount of time spent cycling through different light source combinations. In this way, the eye tracking system may estimate which combination of light sources will produce the lowest amount of occlusion and iteratively project light from the different combinations of light sources in an order that is based upon the estimation. It is to be understood that in other embodiments, the combination of light sources may be selected based upon an amount of occlusion in an image, as described below.

At 210, method 200 includes determining whether unacceptable occlusion exists in the image for each tested light source combination, and at 212, selecting a combination of light sources for performing eye tracking. As indicated at 214, a light source combination may be selected based on an amount of occlusion detected in the image. In some embodiments, the iterative testing of each combination may cease upon identification and selection of a suitable combination, while in other embodiments a full set of combinations may be tested before selecting one. As part of the testing of each combination, for a given light source configuration, glares may either be matched to their corresponding glints, or occlusion metrics may be obtained between the glares and the pupil or glints. In the case of high occlusion (e.g., occlusion above a threshold), the next light source configuration may be chosen from the sequence. The process may then repeat until unoccluded or partially occluded pupil-glints are obtained with high confidence scores. This configuration may then be utilized across future frames until a next occlusion is detected, when the configurations are again cycled through until a suitable light source configuration is again determined.

Method 200 further includes, at 216, projecting light via the selected combination of light sources, and at 218 tracking a gaze location of one or more eyes by detecting light from the light sources as reflected from the eye(s). Further, at 220, method 200 includes performing an action responsive to the eye tracking. The eye tracking may be used to perform any suitable action. For example, the eye tracking may be utilized to detect eye gestures, to detect position signals for a graphical user interface, etc.

Figure 3:
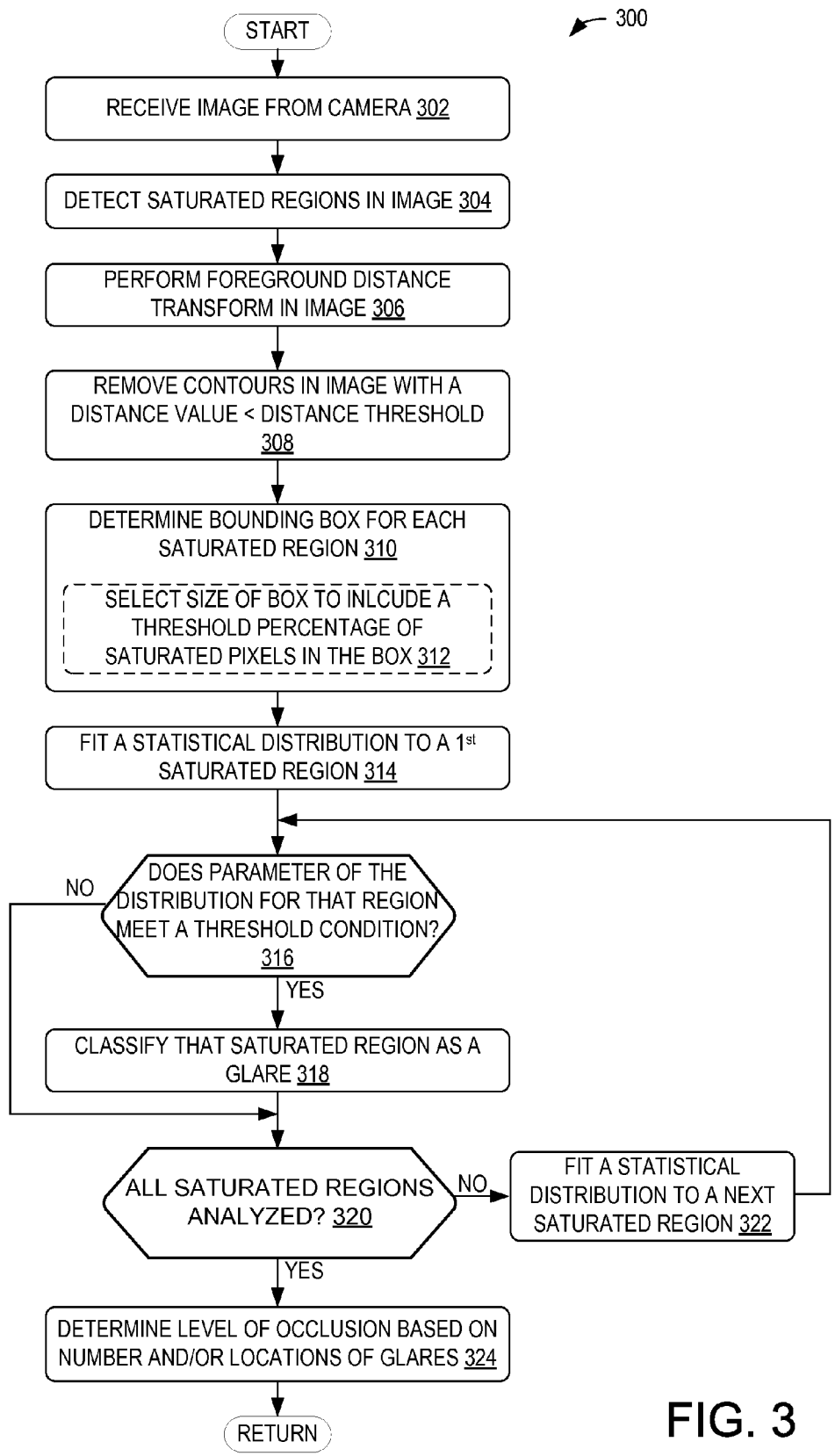
FIG. 3 is a flow diagram depicting an embodiment of a method of classifying reflections in an image from an eye tracking system.

The determination of unacceptable amounts of occlusion of eye glint reflections by glares be determined in any suitable manner. FIG. 3 shows a flow diagram depicting an example embodiment of a method 300 for classifying reflections and/or glare or other interference in images captured by a camera of an eye tracking system. It will be understood that method 300 may be performed by a computing device, such as computing device 104 of FIG. 1, configured to process images in an eye tracking system.

At 302, method 300 includes receiving image data from a camera. The camera may be integrated in a computing device or externally/remotely positioned relative to the computing device. Method 300 further includes, at 304, detecting saturated regions in the received image. For example, the image may be analyzed to determine pixels in the image with a saturation value that is higher than a threshold.

As glares may result from specular reflections from glasses or other smooth structures, the glares may have highly saturated cores, similar to the intensity distribution of the light source itself. As such, glares formed from the light projected from light sources used in the eye tracking system may have a pattern of high intensity at the center, which dissipates abruptly moving away from the center, sometimes resulting in the appearance of flares. From such properties, glares formed from reflections of projections from the light sources may be differentiated from reflections of light off of the user's eye(s) and from other diffused reflections caused due to the presence of other IR sources in the surroundings.

Figure 4:
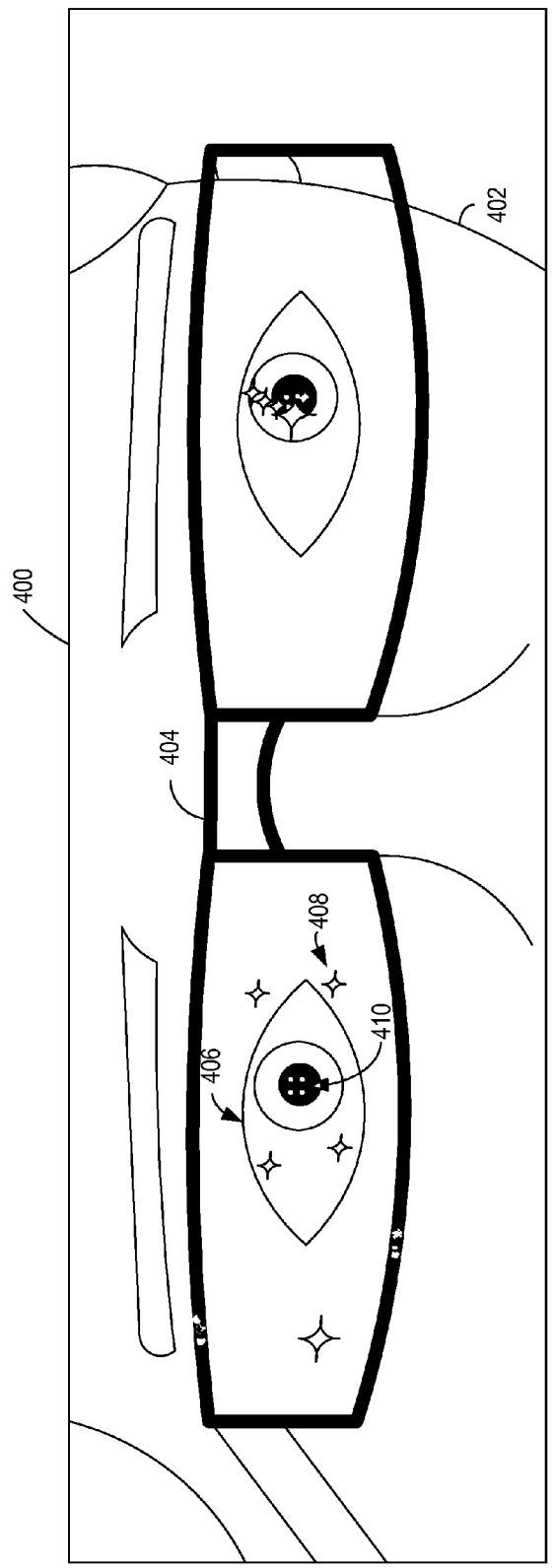
FIG. 4 shows an example image captured by an eye tracking system according to an embodiment of the present disclosure.

FIG. 4 shows an example depiction of an image 400 captured by a camera of an eye tracking system, and shows a view of a user 402 wearing glasses 404. Light the eye tracking system light sources (as well as ambient light sources) may be reflected by the glasses 404, as well as by a pupil of an eye 406 of the user 402. Such reflections from the glasses 404 may result in glares 408, while reflections from the eye may result in glints 410, illustrated as four uniformly spaced dots in a region of the pupil of eye 406.

While the glints 410 appear as small, substantially circular dots, the glares 408 may have a flared, star-like shape.

Returning to FIG. 3, method 300 may include identifying and selecting saturated pixels of the image, and performing a foreground distance transform of the saturated pixels of the image, as indicated at 306, such that an intensity of a pixel after the foreground distance transform is a function of a distance from the boundary of the reflection. This may help to provide an indication of contours of glare candidates based upon a size of a saturated region and/or the contours of the saturated region. For example, a saturated region that is larger than a threshold size may be considered to be a glare candidate, while saturated regions that are smaller than a threshold size may not be considered to be a glare candidate.

Figure 5:
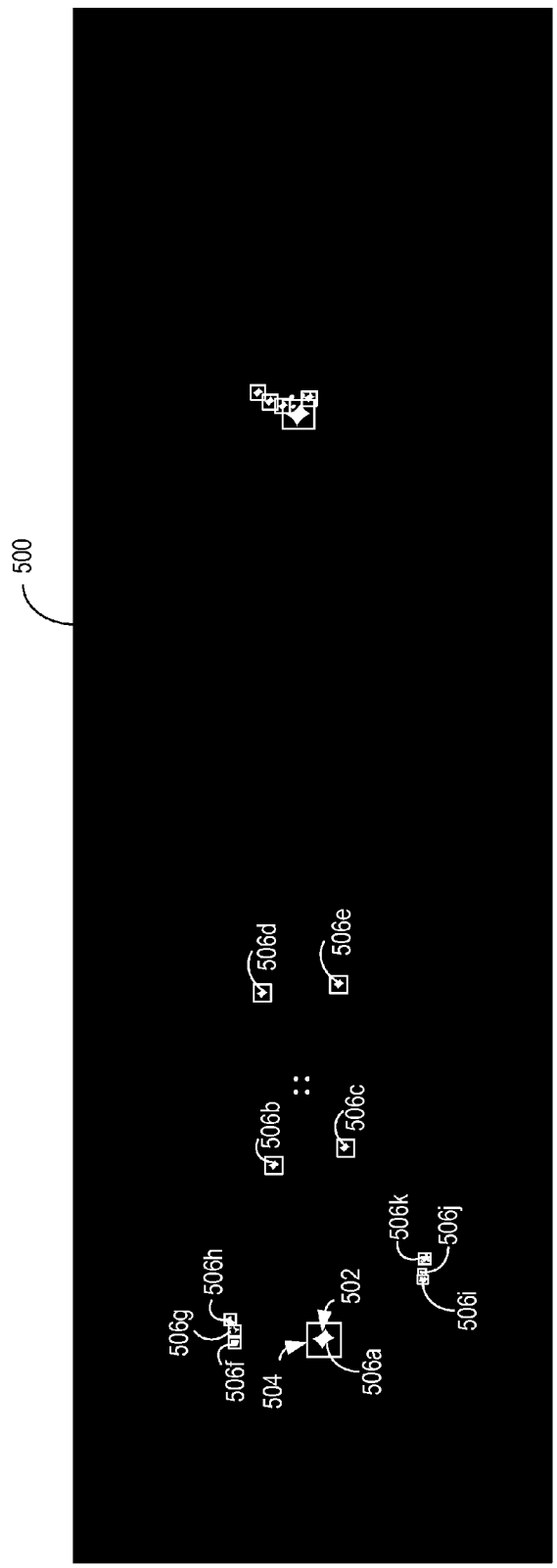
FIG. 5 shows an example of an image captured by an eye tracking system that is processed to identify saturated regions of the image according to an embodiment of the present disclosure.

At 308, method 300 includes removing noise in the image, for example, by removing contours with a distance value that is lower than a distance threshold. In this way, the flared contours of the glares/glare candidates may be smoothed. Further, at 310, method 300 includes determining a bounding box for each remaining saturated region (e.g., the cores of the glares/glare candidates determined at 308). The size of the bounding box may be selected to have a value that enables the box to include a percentage of thresholded saturated pixels, as indicated at 312. For example, a bounding box may be formed around a core of a glare/glare candidate and a size of the bounding box may be increased until the percentage of saturated pixels in the bounding box exceeds some threshold. This resizing may help to ensure that a box is placed around each saturated region. In case of a glare, the box includes a saturated center, while in case of false positives (e.g., non-glares), saturated pixels are spread randomly throughout the box. Turning briefly to FIG. 5, a processed version of the image 400 of FIG. 4 is shown, in which saturated regions 502 (e.g., glare candidates) are surrounded by bounding boxes 504.

Returning to FIG. 3, method 300 includes, at 314, fitting a statistical distribution to a first saturated region. For example, a Gaussian model or other statistical distribution model may be fit to detected glare centers to form normalized distribution of saturated pixels in a region of the glare candidates. A parameter of the fit of the statistical distribution for each saturated region/glare candidate then may be compared to a threshold condition. For example, a Gaussian modeling error may be determined for the Gaussian model fit to that saturated region, and a comparison of the error to a threshold error may be determined at 316. If the parameter meets the threshold (e.g., if the modeling error is below a threshold), then it may be determined at 318 that the region is a glare, and the method may proceed to 320, where it is determined whether all saturated regions have been analyzed. For example, glare candidates 506a, 506b, 506c, 506d, and 506e in FIG. 5 may be classified as glares due to the distribution of saturated pixels within the associated boxes exhibiting glare-like features, such as the concentration of saturated pixels in the central region and flares protruding at regularly spaced peripheral regions. Where it is determined at 316 that the parameter does not meet the threshold, then the method may proceed to 320 without classifying the saturated region as a glare (e.g., glare candidates 506f, 506g, 506h, 506i, 506j, and 506k may not be classified as glares due to a lack of a saturated core and/or absence of other glare features).

At 320, if it is determined that all saturated regions have not been analyzed (e.g., "NO" at 320), then method 300 comprises iteratively performing the processes of 316, 318 and 320 until all saturated regions have been analyzed. If all saturated regions have been analyzed (e.g., "YES" at 320), then method 300 comprises, at 324, to determine a level of occlusion based on a number and/or locations of saturated regions classified as glares. For example, a level of occlusion may be based upon a size of the glares, the number of the glares, and/or how close the glares are to a pupil of the eye/glints reflected from the pupil of the eye.

The various thresholds described above with regard to method 300 (e.g., the distance threshold at 308, the threshold percentage at 312, and the threshold condition at 316) may be predetermined and/or selected based upon statistical data. In additional or alternative embodiments, one or more of the thresholds may be determined via a learning algorithm (e.g., utilizing a classifier). For example, determining the threshold(s) via the learning algorithm may include dynamically altering the threshold(s) over time based upon measured/recorded data for a particular user, environment, lighting arrangement, and/or other suitable condition. Upon determining the thresholds using a classifier, a number of other features (e.g., a quadratic fit error, a position relative to eye corners, dissipation gradient, etc.) may be added to optimize the separation between the glares and the non-glares in the analyzed image.

Figure 6A:
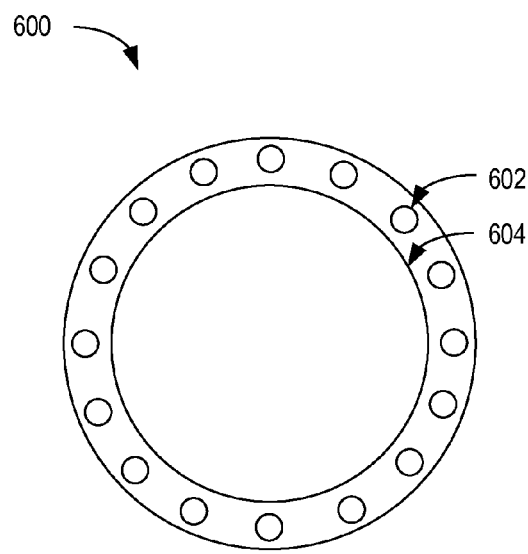
FIGS. 6A and 6B show two views of an example light source arrangement for an eye tracking system according to an embodiment of the present disclosure.
Figure 6B:
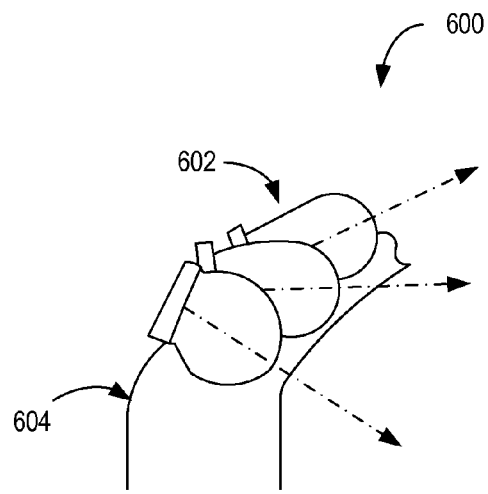

FIGS. 6A and 6B show different views of an example light source arrangement 600 of an eye tracking system. In the front view of 6A, the individual light sources 602 are illustrated as being arranged around a housing structure 604. In some embodiments, the housing structure 604 may include, be integrated within, and/or be mounted to a camera of the eye tracking system. In other embodiments, the housing structure 604 may be configured to be mounted onto other elements. As illustrated, each light source 602 may be positioned in a different location relative to other light sources. In this way, light projected from each light source 602 may be directed to a different location and/or arrive at a particular location at a different angle than light projected from other light sources in the light source arrangement 600. This may allow different combinations of light sources to be used to form reflections from the eye to avoid occlusions from glares, as described above.

Further, as shown in the oblique view of the light source arrangement 600 illustrated in FIG. 6B, one or more of the light sources 602 may be oriented differently from other light sources in the arrangement. The dashed arrows indicate the direction of light emitted from each of the light sources 602. In this way, light projected from each light source 602 may be directed to a different location and/or arrive at a particular location from a different angle than light projected from other light sources in the light source arrangement 600.

Occlusion of pupil glints in eye tracking images may be based on classifying reflections on the optical structure based on their features like location, size, intensity distribution, and mapping to the light sources. By providing a light source arrangement including light sources that direct light from different locations/angles, the light sources may be iteratively turned on/off to generate different combinations of light source projections in an eye tracking system. Analyzing images captured during projection of light from each combination of light sources may identify glares (e.g., determine a location of glares relative to the eye) and/or match glares to particular light sources/light source combinations. Accordingly, a light source combination that produces unoccluded pupil glints that are obtained with a high confidence score, a fewest number of occlusions of the eye/glints reflected from the eye, and/or otherwise produces a suitable eye tracking image may be selected for performing eye tracking. Selecting a particular light source combination for a given user/environment may enable the system to operate in a broader range of conditions, including conditions in which optical structures, such as glasses, are present between the eye tracking camera/light sources and the eye being tracked.

In some embodiments, the methods and processes described herein may be tied to a computing system of one or more computing devices. In particular, such methods and processes may be implemented as a computer-application program or service, an application-programming interface (API), a library, and/or other computer-program product.

Figure 7:
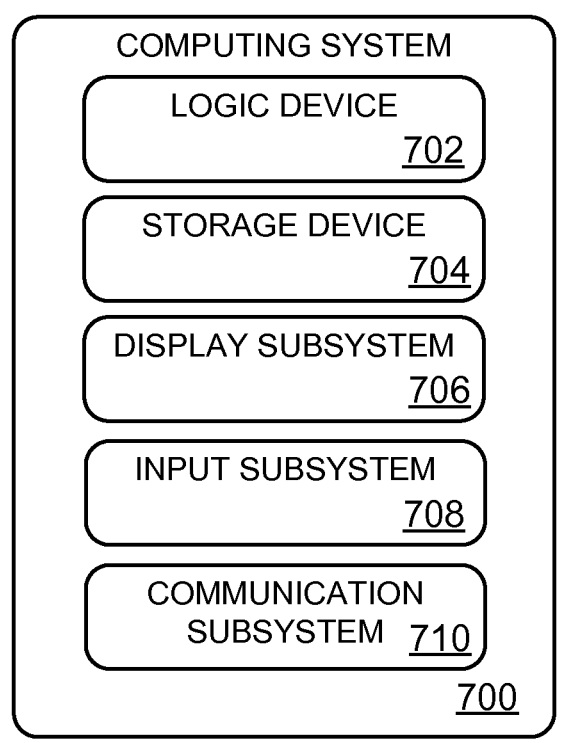
FIG. 7 is a block diagram of an embodiment of a computing system.

FIG. 7 schematically shows a non-limiting embodiment of a computing system 700 that can enact one or more of the methods and processes described above. Computing system 700 is shown in simplified form. Computing system 700 may take the form of one or more personal computers, server computers, tablet computers, home-entertainment computers, network computing devices, gaming devices, mobile computing devices, mobile communication devices (e.g., smart phone), wearable computing devices, and/or other computing devices. For example, computing system 700 may be an example of computing device 104 of FIG. 1 and/or may perform the methods described in FIGS. 2 and 3.

Computing system 700 includes a logic device 702 and a storage device 704. Computing system 700 may optionally include a display subsystem 706, input subsystem 708, communication subsystem 710, and/or other components not shown in FIG. 7.

Logic device 702 includes one or more physical devices configured to execute instructions. For example, the logic device may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic device 702 may include one or more processors configured to execute software instructions. Additionally or alternatively, the logic device may include one or more hardware or firmware logic devices configured to execute hardware or firmware instructions. Processors of the logic device may be single-core or multi-core, and the instructions executed thereon may be configured for sequential, parallel, and/or distributed processing. Individual components of the logic device optionally may be distributed among two or more separate devices, which may be remotely located and/or configured for coordinated processing. Aspects of the logic device may be virtualized and executed by remotely accessible, networked computing devices configured in a cloud-computing configuration.

Storage device 704 includes one or more physical devices configured to hold instructions executable by the logic device to implement the methods and processes described herein. When such methods and processes are implemented, the state of storage device 704 may be transformed—e.g., to hold different data.

Storage device 704 may include removable and/or built-in devices. Storage device 704 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage device 704 may include volatile, nonvolatile, dynamic, static, read/write, read-only, random-access, sequential-access, location-addressable, file-addressable, and/or content-addressable devices.

It will be appreciated that storage device 704 includes one or more physical devices. However, aspects of the instructions described herein alternatively may be propagated by a communication medium (e.g., an electromagnetic signal, an optical signal, etc.) that is not held by a physical device for a finite duration.

Aspects of logic device 702 and storage device 704 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 700 implemented to perform a particular function. In some cases, a module, program, or engine may be instantiated via logic device 702 executing instructions held by storage device 704. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, display subsystem 706 may be used to present a visual representation of data held by storage device 704. This visual representation may take the form of a graphical user interface (GUI). As the herein described methods and processes change the data held by the storage device, and thus transform the state of the storage device, the state of display subsystem 706 may likewise be transformed to visually represent changes in the underlying data. Display subsystem 706 may include one or more display devices utilizing virtually any type of technology. Such display devices may be combined with logic device 702 and/or storage device 704 in a shared enclosure, or such display devices may be peripheral display devices.

Input subsystem 708 may comprise or interface with one or more user-input devices such as an eye tracking system (e.g., the eye tracking system of computing device 104 in FIG. 1), keyboard, mouse, touch screen, handwriting pointer device, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. For example, the input subsystem may comprise an eye tracking system and/or a portion of an eye tracking system utilized to perform the methods 200 and/or 300 of FIGS. 2 and 3.

When included, communication subsystem 710 may be configured to communicatively couple computing system 700 with one or more other computing devices. Communication subsystem 710 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 700 to send and/or receive messages to and/or from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. An eye tracking system comprising:
a plurality of light sources;
a camera configured to capture an image of light from the light sources as reflected from an eye;
a logic device; and
a storage device storing instructions executable by the logic device to
acquire frames of eye tracking data by iteratively projecting light from different combinations of light sources of the plurality of light sources and capturing an image of the eye during projection of each combination;
determine occlusion in the image by detecting one or more saturated regions in the image, determining a bounding box for each saturated region based upon one or more criteria, and classifying a saturated region within a bounding box as a glare if a parameter of the saturated region meets a condition;
select a selected combination of light sources for eye tracking based on the determination of occlusion detected in the image arising from a transparent or semi-transparent optical structure positioned between the eye and the camera; and
project light via the selected combination of light sources for eye tracking.

2. The eye tracking system of claim 1, wherein iteratively projecting light from different combinations of light sources includes iteratively projecting light from the different combinations of light sources in an order that is based upon a predicted occlusion for each of one or more combinations.

3. The eye tracking system of claim 2, further comprising detecting a head pose, and determining the predicted occlusion based upon the head pose.

4. The eye tracking system of claim 1, further comprising designating a saturated point in an image as a glare and matching the glare with a selected light source in a first combination of light sources based on a determination of whether the glare is present in a next image captured during projection of a second, different combination of light sources that does not include the selected light source.

5. The eye tracking system of claim 1, wherein iteratively projecting light from different combinations of light sources includes projecting light from a combination including a lesser number of light sources before projecting light from a combination including a greater number of light sources.

6. The eye tracking system of claim 1, wherein iteratively projecting light from different combinations of light sources includes projecting light from a combination including a greater number of light sources prior to projecting light from a combination including a lesser number of light sources.

7. The eye tracking system of claim 1, wherein the plurality of light sources includes a plurality of infrared light emitting diodes (LEDs).

8. The eye tracking system of claim 1, wherein the plurality of light sources includes four infrared light emitting diodes (LEDs) and iteratively projecting light from different combinations of light sources comprises iteratively projecting light from different LEDs or combinations of the four infrared LEDs.

9. The eye tracking system of claim 1, wherein iteratively projecting light from different combinations of light sources comprises projecting light from all of the plurality of light sources during a first iteration and projecting light from one or more subsets of the plurality of light sources during one or more other iterations.

10. The eye tracking system of claim 1, wherein one or more of the plurality of light sources are oriented differently from one another, and wherein iteratively projecting light from different combinations of light sources comprises iteratively projecting light from different combinations of light sources having different combinations of orientations.

11. The eye tracking system of claim 1, wherein the instructions are further executable to determine occlusion in the image by
fitting a statistical distribution to each saturated region within each bounding box, and
classifying a saturated region within a bounding box as a glare if a parameter of the statistical distribution fit to the saturated region meets a condition.

12. A method of tracking eye movements, the method comprising:
acquiring frames of eye tracking data by iteratively projecting light from different combinations of light sources and capturing an image of an eye with a camera during projection of each combination;
determining an amount of occlusion in the image by detecting one or more saturated regions in the image, determining a bounding box for each saturated region, and classifying a saturated region within a bounding box as a glare if a parameter of the saturation region meets a threshold condition;
selecting a selected combination of light sources for eye tracking based on the amount of occlusion detected in the image arising from a transparent or semi-transparent optical structure positioned between the eye and the camera; and
projecting light via the selected combination of light sources for eye tracking.

13. The method of claim 12, wherein determining the amount of occlusion further comprises fitting a statistical distribution to each saturated region within each bounding box, and classifying a saturated region within a bounding box as a glare if a parameter of the statistical distribution fit to the saturation region meets a threshold condition.

14. The method of claim 13, wherein determining a bounding box for each saturated region includes increasing a size of the bounding box until a percentage of saturated pixels in the bounding box meets a threshold.

15. The method of claim 13, wherein the amount of occlusion in the image is determined as a function of one or more of the amount, size, and location of each classified region classified as a glare.

* * * * *